United States Patent
Pelati

(10) Patent No.: US 11,661,496 B2
(45) Date of Patent: *May 30, 2023

(54) ADDITIVES TO REMEDIATE DVB CROSS-LINKING AND INSOLUBLE POLYMER FORMATION IN THE STYRENE PROCESS

(71) Applicant: FINA TECHNOLOGY, INC., Houston, TX (US)

(72) Inventor: Joseph Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/811,083

(22) Filed: Mar. 6, 2020

(65) Prior Publication Data
US 2020/0283597 A1 Sep. 10, 2020

Related U.S. Application Data

(60) Provisional application No. 62/814,659, filed on Mar. 6, 2019.

(51) Int. Cl.
*C08K 5/07* (2006.01)
*C07C 7/20* (2006.01)

(52) U.S. Cl.
CPC ..................... *C08K 5/07* (2013.01)

(58) Field of Classification Search
CPC ............ C07C 5/321; C07C 15/46; C07C 7/20
See application file for complete search history.

(56) References Cited

U.S. PATENT DOCUMENTS

| | | | | |
|---|---|---|---|---|
| 6,835,288 B1 * | 12/2004 | Sutoris | ..................... | C07B 63/04 203/3 |
| 2008/0200616 A1 * | 8/2008 | Tanizaki | ................. | C07B 63/04 525/382 |

FOREIGN PATENT DOCUMENTS

| | | | |
|---|---|---|---|
| CN | 101240169 | † | 8/2008 |
| EP | 0240297 | † | 10/1987 |
| EP | 0240297 A | * | 10/1987 |
| EP | 1813585 | † | 8/2007 |
| GB | 793841 | † | 4/1958 |
| RU | 2290394 | † | 12/2006 |
| WO | WO-02051962 A1 | * | 7/2002 |
| WO | 2012018650 | † | 2/2012 |

OTHER PUBLICATIONS

Machine translation into English of Lartigue et al (WO-02051962-A1) (Year: 2002).*
Santa Cruz Biotechnology, Inc., "1, 5, 7-Triazabicyclo[4.4.0]dec-5-ene (CAS 5807-14-7)", pp. 1-5, Retrieved on Dec. 2, 2020, Santa Cruz Biotechnology, Inc., retrieved from https://www.scbt.com/p/1-5-7-triazabicyclo-4-0dec-5-ene-5807-14-7.†

\* cited by examiner
† cited by third party

*Primary Examiner* — Karuna P Reddy
(74) *Attorney, Agent, or Firm* — Albert Shung

(57) ABSTRACT

A method of reducing the fouling in a process for the production of styrene, the method comprising: introducing an additive into a stream comprising styrene and byproduct divinyl benzene (DVB), wherein the additive comprises: at least one chemical compound comprising one or more functional groups selected from amines, alcohols, aminoalcohols, labile C—C, esters, carbamates, aldehydes, ketones, acids, acetates, benzoates, labile hydrogen, and combinations thereof, and having a boiling point greater than or equal to 170° C. and within 10, 20, 30, 40, 50, or 60° C. of the boiling point of divinyl benzene (DVB) (which is 195° C.), wherein the at least one chemical compound is active to inhibit divinyl benzene (DVB) crosslinking. A system for carrying out the method is also provided.

13 Claims, 6 Drawing Sheets

ADDITIVES TO REMEDIATE DVB CROSS-LINKING AND INSOLUBLE POLYMER FORMATION IN THE STYRENE PROCESS

CROSS-REFERENCE TO RELATED APPLICATIONS

This application claims the benefit of U.S. Provisional Application No. 62/814,659, filed Mar. 6, 2019, which is incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This disclosure relates to the production of styrene monomer. More particularly, the disclosure relates to reducing the polystyrene fouling encountered in the production of styrene monomer. Still more particularly, the disclosure relates to reducing the amount of insoluble polystyrene polymer formed during styrene production, via an additive comprising at least one chemical component having a boiling point near that of divinyl benzene (DVB) and having sufficient chemical activity to inhibit DVB cross-linking of polystyrene.

BACKGROUND

Styrene, a raw material for major polymer products such as polystyrene, acrylonitrile butadiene styrene, styrene butadiene rubber, and others, is consumed in great quantities annually, being one of the representative general-purpose monomer products. It is well-known that styrene can be prepared by dehydrogenating ethylbenzene (EB) in the presence of superheated water vapor, i.e. steam, on a dehydrogenation catalyst bed in a reactor. Styrene manufacturing plants generally utilize a reaction system comprising two or three adiabatic reactors connected in series, in conjunction with a number of furnaces and heat exchangers.

Conventional manufacturing of styrene, for example via EB dehydrogenation, produces a crude styrene stream that typically contains about 60% styrene. Purification by distillation encounters challenges due to the thermal self-initiation of polymerization by styrene that can occur at a significant rate above 80° C. Styrene boils at 145° C., so distillation is generally carried out at lower pressure and temperature with the addition of polymerization inhibitors (also called antipolymerization agents or polymerization retarders). In order to control unwanted monomer degradation and/or unwanted formation of polystyrene polymer during styrene manufacture, a polymerization retarder is commonly added to the process. Typical products used for this purpose are dinitrophenols such as DNOC (di-nitro-ortho-cresol) or DNBP (di-nitro-sec-butyl-phenol) as well at true inhibitors such as substituted tetramethylpiperidene-1-oxyl species. Despite being effective in controlling styrene polymerization, these retarders can be highly toxic and/or rather costly. The true inhibitors are rapidly consumed and may not be effective in some areas.

Another complication is due to the ubiquitous by-product, divinyl benzene (DVB). DVB is a potent cross-linking agent that can lead to the production of insoluble DVB cross-linked polystyrene polymer (also referred to herein as insoluble polymer and/or DVB cross-linked polymer). Substantial amounts of insoluble polymer are often observed in styrene distillation systems even with the use of conventional distillation inhibitors. Insoluble polymer fouling in styrene production plants can cause issues such as flow restrictions, reduced heat exchange and loss of distillation column performance. The use of modern anti-polymerization inhibitors/retarders, even with high dosages, has not eliminated the formation of insoluble polymer. DVB has a boiling point of 195° C. and may concentrate in hot, liquid form in areas where styrene and EB remain in the gas phase. Such areas could be locations where insoluble polymer could initiate. It is feasible that cross-linked polymer radical masses form in such locations. After formation, these insoluble polymer 'seeds' could migrate to other areas where they can settle and form large deposits of insoluble polymer over time. Deposits of insoluble polymer are thus an issue for conventional styrene production.

Accordingly, there exists a need for improved methods of styrene production and/or purification whereby insoluble polymer formation is inhibited.

SUMMARY

Herein disclosed is a method of reducing the fouling in a process for the production of styrene, the method comprising: introducing an additive into a stream comprising styrene and byproduct divinyl benzene (DVB), wherein the additive comprises: at least one chemical compound comprising one or more functional groups selected from amines, alcohols, amino-alcohols, labile C—C, esters, carbamates, aldehydes, ketones, acids, acetates, benzoates, labile hydrogen, and combinations thereof, and having a boiling point greater than or equal to 170° C. and within 10, 20, 30, 40, 50, or 60° C. of the boiling point of divinyl benzene (DVB) (which is 195° C.), wherein the at least one chemical compound is active to inhibit divinyl benzene (DVB) crosslinking.

Also disclosed herein is an additive for reducing the fouling in a process for the purification of a crude styrene comprising styrene and byproduct divinyl benzene (DVB), the additive comprising: at least one chemical compound comprising one or more functional groups active to inhibit divinyl benzene (DVB) crosslinking, and having a boiling point greater than or equal to 170° C. and within 10, 20, 30, 40, 50, or 60° C. of the boiling point of DVB, which is 195° C.; and a polymerization inhibitor having a boiling point of greater than that of the at least one chemical compound.

Also disclosed herein is a composition comprising: a crude styrene stream comprising styrene and by-product divinyl benzene (DVB); and an additive comprising at least one chemical compound comprising one or more functional groups active to inhibit DVB crosslinking, and having a boiling point in the range of from 170° C. to 270° C., from 170° C. to 230° C., from 170° C. to 220° C., or from 170° C. to 195° C.

Also disclosed herein is a system for the production of styrene via dehydrogenation of ethylbenzene (EB), the system comprising: one or more dehydrogenation reactors operable to contact EB and steam with a dehydrogenation catalyst under dehydrogenation conditions to yield a crude styrene effluent comprising styrene and byproduct divinyl benzene (DVB); a heat exchange apparatus configured to reduce the temperature of the crude styrene effluent; a separations apparatus configured to separate offgas and condensate from the cooled crude styrene effluent and thus provide a dehydrogenation mixture; a distillation section operable to separate the dehydrogenation mixture into one or more streams comprising benzene, toluene, ethylbenzene, or a combination thereof, a tar stream, and a stream comprising styrene; an oxidation unit configured to produce, via oxidation of the tar stream, at least one chemical compound comprising one or more functional groups active to inhibit divinyl benzene crosslinking, and having a boiling point greater than or equal to 170° C. and within 10, 20, 30, 40, 50, or 60° C. of the 195° C. boiling point of DVB; and one or more recycle lines whereby the at least one chemical compound can be combined with the crude styrene effluent, the cooled crude styrene effluent, the dehydrogenation mixture, a feed, recycle, or reflux to a distillation column of the distillation section, or a combination thereof.

Also disclosed herein is a method of reducing the fouling in a process for the production of styrene, the method comprising: producing, via oxidation of a crude styrene, a styrene tar stream, or a combination thereof, at least one chemical compound active to inhibit divinyl benzene (DVB) crosslinking, comprising one or more functional groups selected from amines, alcohols, amino-alcohols, labile C—C, esters, carbamates, aldehydes, ketones, acids, acetates, benzoates, labile hydrogen, and combinations thereof, and having a boiling point greater than or equal to 170° C. and within 10, 20, 30, 40, 50, or 60° C. of the boiling point of divinyl benzene (DVB) (which is 195° C.); and introducing the at least one chemical compound into a stream comprising styrene and byproduct divinyl benzene (DVB), whereby divinyl benzene (DVB) crosslinking is inhibited.

BRIEF DESCRIPTION OF THE DRAWINGS

The detailed description will reference the drawings briefly described below, wherein like reference numerals represent like parts.

DETAILED DESCRIPTION

Overview

Figure 1:
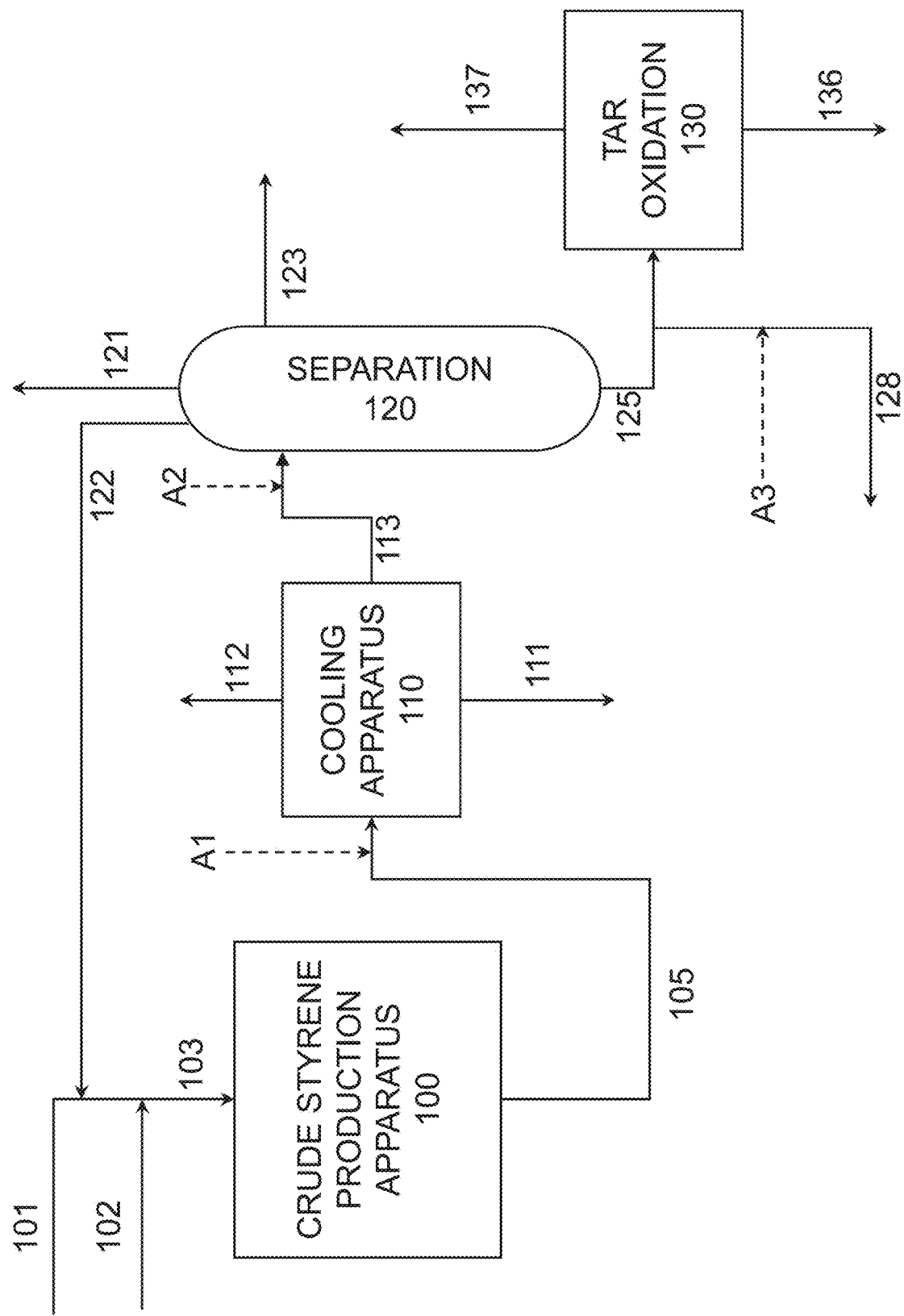
FIG. 1 is a process flow diagram of a styrene production system according to an embodiment of this disclosure.

It should be understood at the outset that although illustrative implementations of one or more aspects are illustrated below, the disclosed additives, compositions, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

As noted above, styrene produced by the high temperature dehydrogenation of ethylbenzene (EB) contains low-level by-products, such as divinyl benzene (DVB), which can lead to insoluble polymer fouling. Deposits of insoluble, DVB-crosslinked polymer can be a serious issue for styrene plants. The issue is exacerbated by the fact that the run lengths for such plants may last three years of longer. Herein disclosed are additives that can reduce or inhibit such insoluble polymer formation, along with the concomitant fouling (e.g., DVB fouling effects), compositions comprising such additives, and methods of reducing the fouling encountered during production and/or purification of styrene. Such additives comprise one or more components having boiling points near that of DVB and having sufficient chemical activity to inhibit DVB from forming insoluble polymer (e.g., to inhibit the formation of DVB cross-linked polystyrene).

Standard polymerization inhibitors appear to suppress DVB reactions when present, however, such polymerization inhibitors are typically expensive, toxic, and high-boiling (e.g., boiling above 200° C. at atmospheric pressure). It has been discovered that an additive as described herein comprising at least one chemical compound (also referred to herein as a 'chemical component') having a boiling point near that of DVB can be effective to address possible sites of condensation and reaction of DVB. By having a boiling point near that of DVB (and lower than that of conventional polymerization inhibitors), the chemical component(s) can remain with (or 'follow') the DVB during the styrene purification process. Without wishing to be limited by theory, such sites of DVB condensation may be a source of 'seed' polymer that leads to insoluble polymer deposits, and additives as described herein comprising a chemical component(s) with appropriate properties for interacting with DVB and following the DVB (i.e., remaining with the DVB throughout most of the styrene purification/post-production processing) may reduce such seeding, along with the resulting insoluble polymer fouling.

Unless otherwise noted, boiling points listed herein are standard boiling points at 1 atm pressure. In embodiments, the at least one chemical compound boiling near that of DVB has a boiling point that is within 5, 10, 20, 30, 40, 50, or 60° C. of the boiling point of DVB, which is 195° C., and sufficiently higher than the boiling point of styrene (e.g. 170° C.) to allow effective separation from styrene. That is, in embodiments, the at least one chemical component has a boiling point in the range of from 190° C. to 200° C., from 185° C. to 205° C., from 175° C. to 215° C., from 170° C. to 225° C., from 170° C. to 235° C., from 170° C. to 245° C., or from 170° C. to 255° C. In embodiments, the at least one chemical component has a boiling point less than or equal to that of DVB, i.e., less than or equal to 195° C. In embodiments, the at least one chemical component has a boiling point greater than or equal to that of styrene, i.e., greater than or equal to 145° C. and desirably higher than 170° C. to allow effective separation by distillation. In embodiments, the at least one chemical compound has a boiling point of less than or equal to about 260° C., 250° C., 240° C., 230° C., 220° C., 210° C., 200° C., or 195° C., has a boiling point of greater than or equal to about 170° C., 180° C., 190° C., 200° C., 210° C., 220° C., or 230° C., or some range therein delineated.

The at least one chemical component also comprises one or more functional groups such that it is active to inhibit DVB crosslinking. As used herein, a chemical component is 'active to inhibit DVB crosslinking' if purification of a crude styrene comprising styrene and DVB in the presence of the chemical component produces less insoluble polymer (which may, in instances, be indicated by a reduced decrease in DVB) than the same process absent the at least one chemical component. Such analysis may be performed, for example, via the technique described in Example 1 herein below. A method according to this disclosure may provide for reduced fouling during the production/purification of styrene. Such a reduction in fouling may comprise a reduction in the formation of insoluble polystyrene, soluble polystyrene, or both, relative to the same process absent the additive.

Several different chemical moieties (e.g., labile C—H and C—C bonds, oxygen and nitrogen functional groups) have been found to have the ability to inhibit the undesirable reaction of DVB, and retard DVB crosslinking. In embodiments, the chemical component comprises appreciably active oxygen, such as provided by, without limitation, alcohols, aldehydes, ketones, esters and carbonates. In embodiments, the chemical component comprises reactive hydrogen functional groups, such as provided by, without limitation, strained cyclics and carbonyls with beta hydrogens. In embodiments, the one or more functional groups are selected from amines, alcohols, amino-alcohols, labile C—C, esters, carbamates, aldehydes, ketones, acids, acetates, benzoates, labile hydrogen, glycols, or combinations thereof. In embodiments, the at least one chemical compound is selected from amines, glycols, benzoates, carbamates, or combinations thereof. Without wishing to be limited by theory, a key chemical property, in addition to the aforementioned boiling point, may be a chemical lability sufficient to interfere with radical chain polymerization. Moreover, some species may be able to chemically react with DVB at typical styrene distillation conditions.

Suitable chemical compounds include, without limitation, ethyl lactate, tetralin, acetophenone, propylene glycol, di-propylene glycol, dipropylene glycol methyl ether, transtilbene, N,N-diethyl-1,4,-phenylenediamine, phenylethanol (e.g., 1-phenylethanol), benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, terpineol, or a combination thereof.

Without wishing to be limited by theory, the at least one component may be active to inhibit DVB crosslinking by consuming DVB (e.g., causing incorporation thereof into soluble polymer or otherwise reacting with DVB), preventing its incorporation into radical polymerization, or some other mechanism. For example, as seen in Example 1 herein below, benzaldehyde may react with DVB and thus effectively remove it from the process stream, and alkyl benzoates appear to suppress DVB reactivity by another mechanism. Addition reactions including, but not limited to, the Diels-Alder Reaction may occur to remove DVB from the process.

The herein-disclosed additive may comprise more than one chemical component active to inhibit DVB crosslinking and having a boiling point near that of DVB. For example, in embodiments, the additive comprises one such chemical component having a boiling point below that of DVB (i.e., less than 195° C.), and another such chemical component having a boiling point above that of DVB (i.e., greater than 195° C.). Such an additive mixture may be operable to span vapor pressure regions and thus provide broad coverage for retarding DVB reactivity. Such mixtures containing species having boiling points that are higher and lower than DVB may, for example, provide broad coverage in the condensation areas and distillation columns.

The additive may further enhance overall performance when used with a conventional polymerization inhibitor. In embodiments, an additive of this disclosure thus further comprises a conventional polymerization inhibitor. Generally, such conventional polymerization inhibitors have much higher boiling points than the chemical components described herein. For example, conventional polymerization inhibitors may have boiling points of greater than 195° C., 200° C., 250° C., or 300° C. Such polymerization inhibitors include, without limitation, those comprising dinitrophenols (e.g., DNOC (di-nitro-ortho-cresol) or DNBP (di-nitro-sec-butyl-phenol)), TMPO compounds (e.g., 4-hydroxy-2,2,6,6-tetramethylpiperidine 1-oxyl, (2,2,6,6-tetramethylpiperidin-1-yl)oxyl or (2,2,6,6-tetramethylpiperidin-1-yl)oxidanyl), oximes (e.g., alternative retarder), and the like, available from multiple commercial vendors.

According to embodiments, a method of reducing the fouling in a process for the production of styrene according to this disclosure comprises introducing an additive as described hereinabove into a stream comprising styrene and byproduct divinyl benzene (DVB). In embodiments, the stream comprising styrene and DVB is a crude styrene formed in a reactor configured to produce styrene. The crude styrene may be a product of ethylbenzene (EB) dehydrogenation, whereby EB is dehydrogenated in the presence of overheated water vapor, i.e. steam, as per Equation (1):

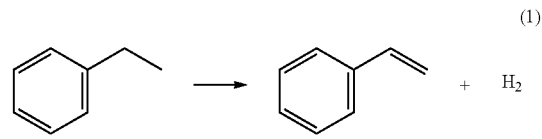

(1)

Systems and methods for producing such a crude styrene product are known in the art, and, in embodiments, the crude styrene is produced via any such known system and method. For example, a multi-stage EB dehydrogenation system and method are described in U.S. Patent App. No. 62/436,653, filed Dec. 20, 2016, which is hereby incorporated herein by reference in its entirety for purposes not contrary to this disclosure. A system and method for producing such a crude styrene are described in more detail herein below.

In embodiments, the additive is introduced at a concentration of 0.001, 0.01, or 0.1 weight percent of the stream comprising styrene and DVB. The stream comprising styrene into which the additive is introduced may be a crude styrene reactor effluent of an EB dehydrogenation reactor, in embodiments. In embodiments, the stream comprising styrene into which the additive is introduced is a feed, recycle, or reflux stream to a distillation column (or other purification unit) of a styrene purification/recovery section downstream of a reactor (e.g., an EB dehydrogenation reactor) in which the crude styrene was produced. As discussed in more detail with reference to FIG. 2 herein below, the distillation column may comprise a distillation column configured for the separation of a tops product comprising EB from a bottoms product comprising styrene, a distillation column configured for the separation of a tops product comprising benzene and toluene from a bottoms product comprising EB and styrene, or a distillation column configured for the separation of a tops product comprising styrene from a bottoms product comprising tar.

Also disclosed herein is a composition comprising such a crude styrene stream comprising styrene and by-product DVB, and an additive as described herein above.

System for the Production/Purification of Styrene

A method for the production of styrene utilizing the herein-disclosed additives will now be described with reference to FIG. 1. FIG. 1 is a process flow diagram of a styrene production system I according to an embodiment of this disclosure. Styrene production system I comprises crude styrene production apparatus 100, cooling, offgas and condensate removal apparatus 110, separation or 'distillation' apparatus 120, and oxidation apparatus 130 as disclosed in this patent. Crude styrene production apparatus 100 is any apparatus operable to produce a crude styrene comprising styrene and DVB from reactants. The reactants may be introduced via one or more reactant feed lines. For example, in the embodiment of FIG. 1, first reactant line 101 and second reactant line 102 are combined to create reactant feed inlet line 103, which is fluidly connected with crude styrene production apparatus 100. The reactant feed may provide an approximately equal mass flow rate of EB and steam, in embodiments. Alternatively, first reactant line 101 and second reactant line 102 can both introduce reactant directly into crude styrene production apparatus 100. Crude styrene is removed from crude styrene production apparatus 100 via crude styrene effluent line 105. As discussed further herein below with reference to FIG. 2, in embodiments, the crude styrene is produced via dehydrogenation of EB. Systems and methods for the production of crude styrene via EB dehydrogenation are known in the art, and may be utilized, in embodiments, to provide the crude styrene. For example, a multi-stage EB dehydrogenation as described in U.S. Patent App. No. 62/436,653 may be employed, in embodiments.

Cooling, offgas and/or condensate removal apparatus 110 is operable to cool by heat exchange, the crude styrene effluent of crude styrene production apparatus 100, which is introduced thereto via crude styrene effluent line 105, and may be referred to herein as simply 'cooling apparatus' or 'condensation zone' 110. Cooling offgas and condensate removal apparatus 110 may also serve to separate an offgas and/or a condensate from the crude styrene, thus providing a crude styrene which has been degassed and from which condensate (e.g., water) has been removed. Offgas line 112 may fluidly connect with cooling apparatus 110, whereby offgas can be removed therefrom, and condensate line 111 may fluidly connect with cooling apparatus 110, whereby condensate can be removed therefrom. In embodiments, offgas line 112 is associated with separations apparatus 120. Separations feed line 113 may fluidly connect cooling apparatus 110 with separation apparatus 120, whereby cooled crude styrene mixture (which may also be degassed and/or dewatered) can be introduced into separation apparatus 120.

Separation apparatus 120 is any apparatus operable to remove one or more byproducts, unreacted reactants, and heavy residue (e.g., tar) from the cooled styrene mixture, thus providing a purified styrene monomer stream. For example, separation apparatus 120 may be configured to separate an unreacted reactant stream (e.g., EB) which may be removed from separation apparatus 120 via unreacted reactant outlet line 122, one or more byproduct streams which may be removed from separation apparatus 120 via one or more byproduct outlet lines 121, and tar which may be removed via tar outlet line 125 from a purified styrene monomer stream, which may be removed from separation apparatus 120 via styrene monomer (SM) outlet line 123. In embodiments, the purified styrene monomer comprises less than 150, 100, or 75 PPM EB. Unreacted reactant outlet line 122 may fluidly connect separations apparatus 120 with crude styrene production apparatus 100, for example via line 101 and/or 103, whereby unreacted reactant may be recycled to produce additional crude styrene.

When crude styrene production apparatus 100 comprises one or more EB dehydrogenation reactors, the unreacted reactant may comprise EB, which may be recycled to crude styrene production apparatus 100, for example, via unreacted reactant outlet line 122, and the byproducts may comprise benzene and/or toluene, which may be removed from separation apparatus 120 via one or more byproduct outlet lines 121.

In embodiments, tar recycle is utilized, whereby at least a portion of the tar in tar outlet line 125 (and/or oxidation residue outlet line 136) is recycled via one or more tar recycle lines 128. In such embodiments, the one or more tar recycle lines 128 may be configured to recycle tar/heavy residue back to separations feed line 113 or into any individual column within separation or distillation apparatus 120.

All or a portion of the styrene tar stream in tar outlet line 125 may be used to feed a tar oxidation unit operation, wherein components in the tar stream can be oxidized to hydrocarbon oxygenates that can be recycled back to the separation section to provide insoluble polymer abatement additives. For instance, without limitation, styrene in the styrene tar can be oxidized to benzaldehyde, acetophenone or phenylethanol; these species can be effective for reducing insoluble polymer fouling. Other species in the tar can also form such oxygenates and provide the same or similar effect. Thus, in embodiments, tar outlet line 125 is fluidly connected with oxidation unit or apparatus 130. Oxidation unit or apparatus 130 is any oxidation apparatus operable to oxidize at least a portion of the tar introduced thereto via tar outlet line 125 to at least one chemical component described hereinabove for use in the herein-disclosed additive. For example, the tar may comprise some latent styrene monomer and/or other monomer/compounds, which may be converted (i.e., oxidized) to form a desirable oxygenated chemical component of an additive as described herein, such as, without limitation, acetophenone, phenylethanol and/or benzaldehyde. In an exemplary embodiment, lab batch reactors at 120° C. have shown the production of 1.4% benzaldehyde, 0.9% acetophenone and 50 ppm of phenylethanol using plant stream samples. It is noted that the oxidation unit operation can be used on the styrene tar and/or another stream from separation section 120 provided the stream comprises oxidizable species.

One or more additive component outlet lines 137 may be configured to remove the at least one additive component from oxidation unit 130, which may be reintroduced elsewhere in styrene production system I as an additive component. The additive component stream in additive component outlet line(s) 137 from the oxidation reaction in oxidation unit 130 may be recycled back to the feed stream to separations (e.g., separations feed line 113) and/or another point within the separations section within separations apparatus 120. For example, as described further herein below, the one or more additive component outlet lines 137 may be configured to be used in the effluent as is or for removal of at least one oxygenated chemical compound from tar oxidation apparatus 130, which may be combined with other additive components and/or introduced into the crude styrene effluent in crude styrene effluent line 105, into the cooled (and/or degassed and/or dewatered) crude styrene effluent in separations feed line 113, a feed, recycle, and/or reflux to a distillation column of the separation apparatus 120, or a combination thereof. An oxidation residue may be used in the effluent as is or removed from oxidation unit or apparatus 130 via oxidation residue outlet line 136. Although not indicated in the Figures, in embodiments, a portion of the styrene monomer, for example in purified styrene monomer outlet line 123 (or elsewhere) can be introduced into an oxidation unit (with or without the EB tar), to produce the oxygenated chemical component(s) for use in an additive as per this disclosure.

As discussed hereinabove, styrene, which has a boiling point of 145° C., thermally self-initiates polymerization in the liquid state (styrene polymerization does not occur in the gas phase), and the polymerization rate can be significant at temperatures above 80° C. The boiling point of DVB is 50° C. higher than the boiling point of styrene and can also thermally self-initiate polymerization, and thus there may be areas in a styrene production plant where DVB can accumulate in high concentrations by condensation. Such areas could be locations where insoluble polymer formation initiates. Two main areas of potential concern have been discovered, and it is within these areas that introduction (and/or the presence) of an additive according to this disclosure may serve particularly useful. A first area is the point where gas phase crude styrene from styrene production reactors is first condensed to liquid. In this area, the higher boiling DVB could liquefy before styrene does, thus providing a location exposed to hot, liquid DVB. A second potential initiation area could be in the distillation columns of downstream separations/purification apparatus where DVB vapor could condense without the presence of inhibitor/retarder. Once produced, such insoluble polymer could attach and grow with time, with the attachment occurring at the point of initiation and/or somewhere downstream therefrom. Insoluble polymer can absorb and hold styrene to facilitate its growth. Accordingly, in embodiments, a method of reducing the fouling in a process for the production of styrene according to this disclosure comprises introducing an additive, as described hereinabove, into one or more streams comprising styrene and byproduct divinyl benzene (DVB) within such a first area (via one or more additive inlet lines A1), within such a second area (via one or more additive inlet lines A2), and/or into another area (via one or more additive inlet lines A3).

For example, as indicated in FIG. 1, an additive according to this disclosure may be introduced into crude styrene effluent line 105 via additive inlet line A1, prior to cooling of the crude styrene effluent in cooling apparatus 110, such that the additive is present within the first area noted above where gas phase crude styrene from styrene production reactors of crude styrene production apparatus 100 is first condensed to liquid. Alternatively or additionally, an additive according to this disclosure may be introduced just prior to or during the purification of the cooled crude styrene, as indicated by additive inlet line A2 of FIG. 1. In this manner, the additive will be present in the second noted area of concern—in the distillation columns of downstream separations/purification apparatus 120 where DVB vapor could condense without the presence of inhibitor/retarder.

Alternatively or additionally, an additive according to this disclosure may be introduced elsewhere, such as, without limitation, into a tar recycle stream, as indicated by additive inlet line A3 of FIG. 1. In such embodiments, one or more additive inlet lines A3 may be configured to introduce an additive according to this disclosure into one or more tar recycle lines 128 configured to recycle tar/heavy residue from tar outlet line 125 (and/or oxidation residue outlet line 136 discussed below) back to separations feed line 113 and/or to any individual column in the separation section.

As the first area (i.e., area at which gaseous crude styrene is first condensed to liquid within cooling apparatus 110) is generally at higher temperatures than the distillation columns of separations apparatus 120, an additive introduced into the first area via an additive inlet line A1 may be disparate from an additive introduced into the second area via an additive inlet line A2 and/or an additive introduced into another area via an additive inlet line A3, in embodiments.

Production of Crude Styrene in Crude Styrene Production Apparatus

In embodiments, the crude styrene comprising styrene and DVB is produced in crude styrene production apparatus 100 via EB dehydrogenation. Such EB dehydrogenation may be performed conventionally as known in the art, with steam dilution, reduced pressure operation, and adiabatic reactors. For endothermic reactions, reheaters are located between the adiabatic reactors. The dehydrogenation reaction may be favored at low pressure, so the reactors are typically operated at reduced pressure (i.e., vacuum conditions) by installing a compressor(s) (e.g., a vacuum compressor(s)) on the effluent line. Conventional three-bed reactor systems are arranged in series, and are common retrofit options for increasing plant capacity.

In embodiments, as described in U.S. Patent App. No. 62/436,653, a first two EB dehydrogenation reactors of a multi-stage dehydrogenation application may be operated in parallel, and the combined product streams thereof are fed to a common third reactor, thus enabling a lowering of the overall reactor pressure, a decrease in energy needs, and/or an increase in product selectivity, while maintaining desirable conversion.

In embodiments, the crude styrene is produced via conventional styrene manufacturing utilizing a reaction system comprising two or three adiabatic reactors connected in series, in conjunction with a number of furnaces and heat exchangers. The styrene can be prepared by dehydrogenating EB in the presence of overheated water vapor, i.e. steam, on a dehydrogenation catalyst bed in a reactor. In the process, EB is mixed in the gas phase with six to twelve times its volume in high temperature steam, and passed over a solid bed of catalyst. Most ethylbenzene dehydrogenation catalysts are based on ferric oxide, promoted by several percent potassium oxide or potassium carbonate.

In the dehydrogenation process, a high conversion rate of ethylbenzene and a high selectivity to styrene, which inhibits the generation of side products such as benzene and toluene, are desirable. Process parameters affecting dehydrogenation performance include reaction temperature, reaction pressure, space velocity, the mixing ratio of steam to hydrocarbon (e.g., ethylbenzene), and etc.

Since the dehydrogenation reaction of ethylbenzene is an endothermic reaction, a higher reaction temperature is advantageous to the reaction. However, when the reaction temperature is excessively high, the selectivity to styrene decreases, and a side-reaction, which generates benzene, toluene, or other byproducts, becomes dominant. Due to the rather great amount of reaction heat, the outlet temperature of a reactor is significantly lower than the inlet temperature of the reactor. To compensate for the temperature drop, conventional dehydrogenation processes employ multiple reactors, and an interstage energy addition is provided between the reactors.

In many reactions, water acts as a catalytic poison, however it is well known that water plays important roles in the dehydrogenation of ethylbenzene. Steam reacts with potassium and iron, generates active sites, supplies latent heat for powering the endothermic reaction, and removes deposited carbon (i.e., coke) that tends to form on the iron oxide catalyst through the water gas shift reaction. The potassium promoter of the catalyst enhances this decoking reaction. The steam also dilutes the reactant and products, shifting the position of chemical equilibrium towards products. Since substantial energy is needed to maintain steam at temperatures above 600° C., processes using the minimum amount of energy are preferred. When an excessive amount of steam is used at high temperature, an important active component of a dehydrogenation catalyst, i.e. potassium, is dissolved and eluted via a reactor outlet. This has been indicated as a main reason for deactivation of the catalyst.

Since the number of resulting product molecules is more than that of reactants, the conversion levels in the dehydrogenation of ethylbenzene decrease as the pressure increases. That is, lower pressure (or ethylbenzene partial pressure) favors the production of styrene by driving the equilibrium to products. It may thus be desirable to operate the EB dehydrogenation under as low a pressure as possible, without imparting too great a capacity load on the compressor(s). When the pressure is reduced, stability is increased due to a decrease in catalyst coking, and selectivity to styrene is also improved due to a relatively decreased extent of side-reactions, which produce byproducts consisting primarily of benzene and toluene. Consequently, pressure reduction is also considered very advantageous in the process, improving both conversion and selectivity. The dehydrogenation reactors can be operated under vacuum to enhance the conversion and selectivity. Typical overall conversions are about 60-63% for two reactors operated in series and 63-70% for three reactors operated in series. Selectivity to styrene is typically 92-97% molar.

Because styrene and ethylbenzene have similar boiling points, their separation requires large distillation towers and high return/reflux ratios. Thus, a desirable conversion may be maintained within the dehydrogenation reactors, thereby reducing the amount of EB that must be separated from the product stream.

Figure 2:
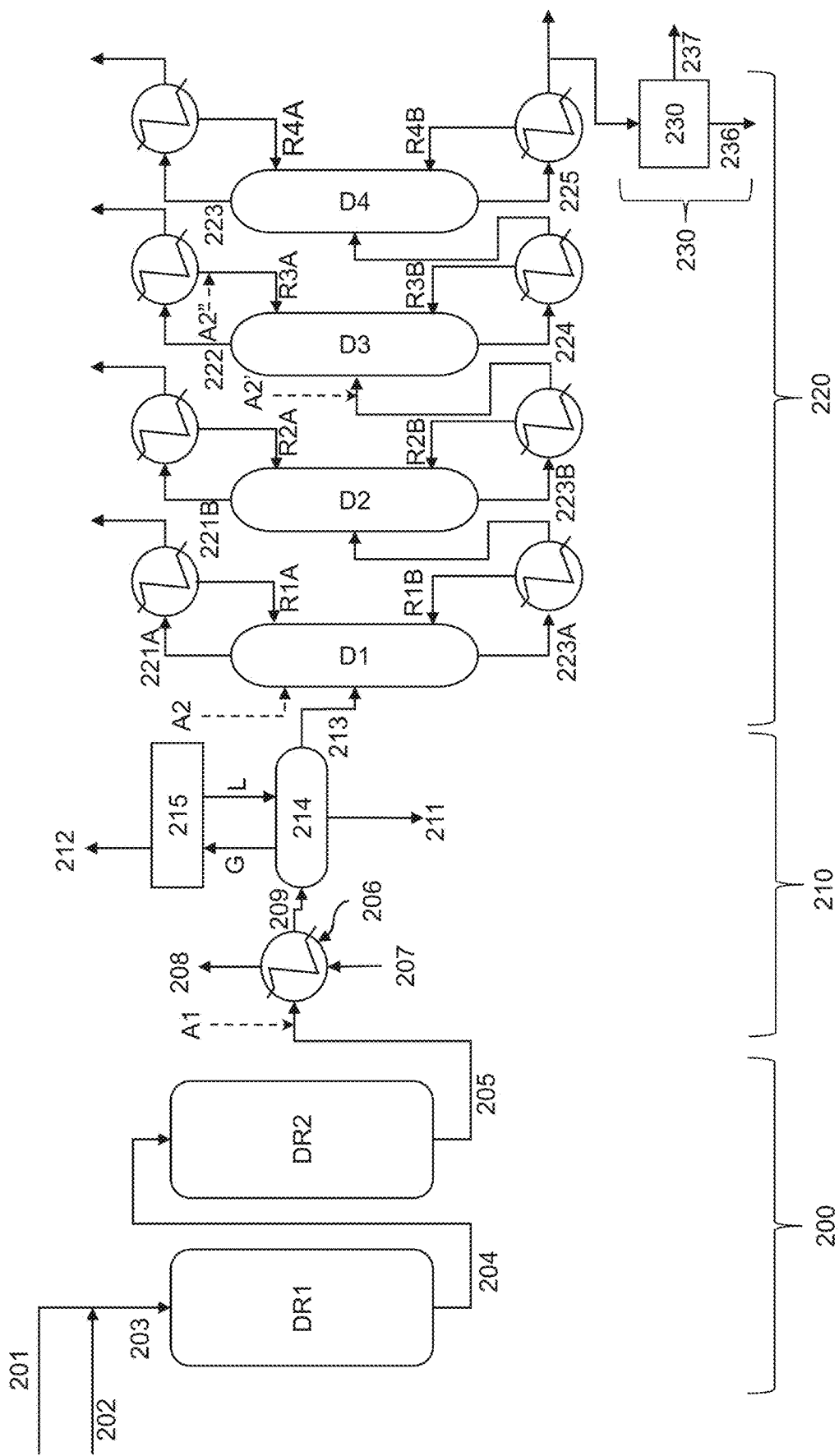
FIG. 2 is a process flow diagram of a styrene production system according to another embodiment of this disclosure.

A styrene production system according to another embodiment of this disclosure will now be described with reference to FIG. 2, which is a process flow diagram of a styrene production system II. Styrene production system II comprises EB dehydrogenation 200, cooling, offgas, and/or condensate removal apparatus 210 (also referred to as 'condensation section 210'), styrene separation/distillation 220, and tar oxidation 230. An EB dehydrogenation system 200 according to this disclosure may comprise any number of dehydrogenation reactors in series and/or in parallel. In embodiments, EB dehydrogenation system 200 comprises three dehydrogenation reactors in series, as described above, while, in other embodiments, dehydrogenation system 200 comprises two dehydrogenation reactors in series upstream of and parallel with a downstream dehydrogenation reactor. In the embodiment of FIG. 2, the crude styrene production system comprises an EB dehydrogenation system 200, comprising a first EB dehydrogenation reactor DR1, in series with a second EB dehydrogenation reactor DR2. EB dehydrogenation reactors DR1 and DR2 are configured for the conversion of EB to styrene via dehydrogenation. During EB dehydrogenation, styrene is produced, as indicated schematically in Eq. 1 above and textually in Eq. 2 below:

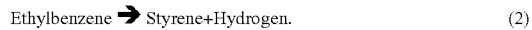

Ethylbenzene ➔ Styrene+Hydrogen.  (2)

Additionally, some benzene and toluene are produced via Eqs. 3 and 4:

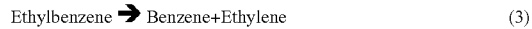

Ethylbenzene ➔ Benzene+Ethylene  (3)

Ethylbenzene+Hydrogen ➔ Toluene+Methane.  (4)

EB in EB reactant line 201, and steam in steam reactant line 202 are combined and introduced into first EB dehydrogenation reactor DR1 via reactant feed inlet line 203. Within first EB dehydrogenation reactor DR1, EB is dehydrogenated in the presence of suitable dehydrogenation catalyst under dehydrogenation conditions, to produce styrene and hydrogen. The product of first EB dehydrogenation reactor DR1 is introduced into second EB dehydrogenation reactor DR2 via first dehydrogenation reactor outlet line 204. Within second EB dehydrogenation reactor DR2, unreacted EB (and/or EB introduced directly into second EB dehydrogenation reactor DR2 (not shown in the embodiment of FIG. 2)) is converted to styrene monomer in the presence of dehydrogenation catalyst.

Dehydrogenation reactors DR1 and DR2 may be any dehydrogenation reactors known to those of skill in the art. As noted above, three reactor systems are an equally viable option. In embodiments, dehydrogenation reactors DR1 and DR2 are adiabatic reactors. Dehydrogenation reactors DR1 and DR2 contain therein dehydrogenation catalyst suitable to catalyze the dehydrogenation of hydrocarbon in the hydrocarbon feed to dehydrogenation product. In embodiments, the dehydrogenation catalyst is a catalyst operable to dehydrogenate ethylbenzene in a hydrocarbon feed to produce a dehydrogenation product comprising styrene. Suitable dehydrogenation catalysts and conditions are known in the art, and will not be described in detail herein. For example, such conditions may include a temperature of about 600° C., a reduced pressure at the outlet of, for example, 7 PSIA (48 kPa), and a large steam dilution (e.g., 6-9 molar ratio of steam to EB). One of skill in the art will find apparent the selection of a suitable dehydrogenation catalyst based on the given reactor conditions. In embodiments, the dehydrogenation catalyst comprises iron (III) oxide, promoted by potassium oxide or potassium carbonate, rare earth oxides and other inorganic performance promoters. In embodiments, the dehydrogenation catalyst comprises a heterogeneous catalyst system suited to operate with steam dilution, reduced pressure and high temperature to overcome the equilibrium constraints and the endothermic reaction.

Crude styrene effluent of EB dehydrogenation apparatus 200 is introduced via crude styrene effluent line 205 into cooling, offgas, and/or condensate removal apparatus 210. Cooling, offgas, and/or condensate removal apparatus 210 is configured to cool the hot dehydrogenation reactor crude styrene effluent from EB dehydrogenation apparatus 200, and may also be configured to remove an offgas and/or condensate therefrom. For example, in the embodiment of FIG. 2, heat exchanger 206 is configured to reduce the temperature of the crude styrene effluent in crude styrene effluent line 205 via heat exchange with a cooling medium introduced into heat exchanger 206 via coolant inlet line 207. Cooled crude styrene is removed from heat exchanger 206 via cooled crude styrene outlet line 209, and heated heat exchange medium removed therefrom via heat exchange outlet line 208. In embodiments, a separator may be utilized to separate a gas and or condensate from the cooled crude styrene. For example, in the embodiment of FIG. 2, separator 214 is configured to separate a gas and a condensate (e.g., comprising condensed water) from the cooled crude styrene introduced thereto via cooled crude styrene outlet line 209. Gas from separator 214 may be introduced into gas compressor 215 via gas line G and compressed liquid returned to separator 214 via liquid line L. Offgas may be removed from compressor 215 via offgas outlet line 212. Condensate may be removed from separator 214 via condensate outlet line 211. An additive of this disclosure may be introduced into condensation section 210, for example into heat exchanger 206 via one or more additive inlet lines A1.

Cooled crude styrene from which offgas and/or condensate may have been removed can be introduced into styrene separation/distillation apparatus 220 (also referred to herein as styrene purification apparatus 220) via separations or 'dehydrogenation mixture' or 'DM' feed line 213. Styrene purification apparatus 220 can comprise any suitable number of distillation columns, as known in the art. Generally, the separations system is operable to separate one or more byproducts (e.g., benzene and/or toluene), unreacted reactant (e.g., EB) and heavy residue (also referred to herein as 'tar') to provide a purified styrene monomer stream. In embodiments, styrene separation system 220 comprises one or more distillation columns configured for the separation of a tops product comprising benzene and toluene from a bottoms product comprising EB and styrene, one or more distillation columns configured for the separation of a tops product comprising benzene from a bottoms product comprising toluene, EB and styrene, one or more distillation columns configured for the separation of a tops product comprising toluene from a bottoms product comprising EB and styrene, one or more distillation columns configured for the separation of a tops product comprising EB from a bottoms product comprising styrene, one or more distillation columns configured for the separation of a tops product comprising styrene from a bottoms product comprising tar, or a combination thereof.

Styrene separation/distillation apparatus 220 of the embodiment of FIG. 2 comprises four distillation columns, including first distillation column D1, second distillation column D2, third distillation column D3, and fourth distillation column D4. First distillation column D1 is configured for the separation of the cooled crude styrene introduced thereto via separations or DM feed line 213 into a tops product comprising benzene (which is removed therefrom via benzene outlet line 221A) and a bottoms product comprising toluene, EB and styrene (which is removed therefrom via first distillation column bottoms product outlet line 223A). Second distillation column D2 is configured for the separation of the first distillation column bottoms product introduced thereto via first distillation column bottoms product outlet line 223A) into a tops product comprising toluene (which is removed therefrom via toluene outlet line 221B and a bottoms product comprising styrene and EB (which is removed therefrom via second distillation column bottoms outlet line 223B. As noted herein, first and second distillation columns D1 and D2 can, in embodiments, may be combined in a single column operable to remove a mixed stream of benzene and toluene overhead. Third distillation column D3 is configured for the separation of the second distillation column bottoms product introduced thereto via second distillation column bottoms product outlet line (223B) into a tops product comprising EB (which is removed therefrom via EB outlet line 222 and a bottoms product comprising styrene (which is removed therefrom via third distillation column bottoms outlet line 224. Fourth distillation column D4 is configured for the separation of the third distillation bottoms product introduced thereto via third distillation column bottoms product outlet line (224) into a tops product comprising styrene monomer (which is removed therefrom via purified styrene outlet line 223 and a bottoms product comprising tar (which is removed therefrom via fourth distillation column bottoms or 'tar' outlet line 225). Optionally, additional columns may be employed to remove latent monomer from the tar stream.

In embodiments according to this disclosure, an additive A2 may be introduced into or with a feed, recycle, and/or reflux stream to a distillation column downstream of an EB dehydrogenation reactor. For example, an additive inlet line A2 may be configured for the introduction of additive into the first distillation column D1 separately from or in combination with the cooled crude styrene in DM feed line 213. Alternatively or additionally, an additive of this disclosure can be introduced into a reflux line of one of the distillation columns, for example, in embodiments, an additive of this disclosure can be introduced into tops reflux R1A and/or bottoms reflux R1B of first distillation column D1, into tops reflux R2A and/or bottoms reflux R2B of second distillation column D2, into tops reflux R3A and/or bottoms reflux R3B of third distillation column D3, and/or into tops reflux R4A and/or bottoms reflux R4B of fourth distillation column D4. By way of example, in the embodiment of FIG. 2, an additive inlet line A2' is configured for the introduction of an additive according to this disclosure into third distillation column D3 (configured for the separation of a tops product comprising EB from a bottoms product comprising styrene) via introduction into the bottoms product of second distillation column D2 extracted therefrom via second distillation column bottoms product outlet line 223B. (Although not shown in the embodiment of FIG. 2, the additive feed line A2' can be introduced directly into third distillation column D3, in embodiments.) By way of further example, in the embodiment of FIG. 2, an additive inlet line A2" is configured for the introduction of an additive according to this disclosure into third distillation column D3 (configured for the separation of a tops product comprising EB from a bottoms product comprising styrene) via introduction into the tops reflux introduced thereto via tops reflux line R3A.

As discussed hereinabove with reference to the embodiment of FIG. 1, a styrene production system according to this disclosure may further comprise oxidation apparatus 230 configured to oxidize at least one component of the tar introduced thereto via fourth distillation column outlet line 225. Oxidation apparatus 230 may be configured to produce at least one oxygenated chemical component suitable for use in an additive of this disclosure, which chemical component can be used as is in the effluent or removed from tar removal apparatus 230 via additive component outlet line 237, and an oxidation residue, which can be removed from tar oxidation apparatus 230 via oxidation residue outlet line 236. Additive component outlet line 237 may fluidly connect tar oxidation apparatus 230 with an upstream apparatus whereby the oxygenated chemical component produced within oxidation apparatus 230 can be introduced into an upstream apparatus as an additive or additive component. Alternatively, as noted above with reference to the embodiment of FIG. 1, oxidation apparatus 230 may be positioned at another location within separation system 220 as desired, and the oxidation stream in additive component outlet line 237 recycled to any suitable point in the separation section.

Although one arrangement of distillation columns is depicted in the embodiment of FIG. 2, one will appreciate that other combinations and/or orders of distillation columns can be utilized to separate the styrene monomer from the crude styrene, and such alternative arrangements are included in the scope of this disclosure. For example, another styrene separation/distillation section could comprise a first distillation column configured to separate a tops product comprising toluene, and benzene, from a bottoms product comprising EB and styrene, a second distillation column configured to separate the bottoms product comprising EB and styrene from the first distillation column into a tops product comprising EB (which may be recycled to the EB dehydrogenation section) and a bottoms product comprising styrene and tar, and a third distillation column configured to separate the bottoms product comprising styrene and tar from the second distillation column into a tops product comprising styrene monomer and a bottoms product comprising tar. In such an embodiment, an additive according to this disclosure may be added to the feed, recycle, and/or reflux to any combination of the distillation columns, for example, to a crude styrene feed to the first distillation column and/or to a reflux to the second distillation column. In other embodiments, multiple distillation columns may be utilized to effect a given separation. By way of nonlimiting example, in embodiments multiple distillation columns are employed to effect the separation of a crude styrene stream from which benzene, toluene and EB have been removed into a purified styrene monomer product and a tar stream (i.e., to separate styrene from tar). Furthermore, various other components (e.g., heaters) may be employed in the system as known in the art (e.g., to maintain a flowable tar). Other arrangements are suitable, and will be readily apparent to those of skill in the art.

As noted above, an additive according to this disclosure introduced within the first area (i.e., the area where gas phase crude styrene from styrene production reactors is first condensed to liquid) via an additive inlet line A1 may be different from an additive introduced into the second area (i.e., in the distillation columns of downstream separations/purification apparatus where DVB vapor could condense without the presence of inhibitor/retarder) via an additive line A2, which may itself be the same or different from an additive introduced elsewhere (e.g., into a tar recycle stream) via an additive inlet line A3. Which of the herein-disclosed additive(s) works best for a given location of injection/introduction can be determined via routine experimentation by one of skill in the art. However, by way of example, an additive introduced into the first area (e.g., via additive inlet line A1) may comprise a higher boiling point chemical component(s) and/or different chemical reactivity (i.e., different functional group(s)) than an additive introduced into the second area (e.g., via an additive inlet line A2, A2', A2"). Similarly, an additive introduced into the first area (e.g., via additive inlet line A1) and/or the second area (e.g., via an additive inlet line A2, A2', A2") may comprise a lower boiling point chemical component(s) and/or different chemical reactivity than an additive introduced into the third area (e.g., via an additive inlet line A3). By way of example, benzoates may be more suitable for use as an additive or additive component for introduction into the second area, but may not be well suited for use in the first area due dissociation in the presence of steam.

In embodiments, an additive is injected into the cooling, offgas, and/or or condensate removal apparatus 110/210 (e.g., via additive line A1) to inhibit or prevent the initiation of insoluble polymer formation due to DVB liquefaction and initiation. Such additive can be injected neat or as a solution in dosages from 1 to 1000 ppm (0.0001 to 0.1 wt %) relative to the organic portion of the process stream. Without limitation, in such embodiments, the additive may be selected from: phenylethanol, terpineol, propylene glycol, ethyl carbamate, acetophenone biphenyl, benzaldehyde, tetralin, diethanolamine, 3-amino-1-propanol, or combinations thereof. In embodiments, an additive introduced into the first area exhibits effective function at higher temperatures, unperturbed by steam, suitable reactivity for condensate conditions, or a combination thereof.

In embodiments, an additive is injected into the feed to or any column of the separation section or apparatus 120/220 (e.g., via additive inlet line(s) A2, A2', A2", or elsewhere) to prevent the initiation of insoluble polymer formation due to DVB liquefaction and initiation. Such additive can be injected neat or as a solution in dosages from 1 to 1000 ppm (0.0001 to 0.1 wt %) relative to the organic portion of the process stream. Without limitation, in such embodiments, the additive may be selected from: propylene glycol, dipropylene glycol, methyl benzoate, benzaldehyde, diethylaminoethanol, acetophenone, DPGME (dipropyleneglycol methyl ether), tetralin, ethylacetoacetate, terpineol, biphenyl, or combinations thereof. In embodiments, an additive introduced into the second area provides suitable boiling point, reactivity sufficient for high styrene/DVB concentrations, acceptable physical properties, or a combination thereof.

In embodiments, an additive introduced into the third area via additive inlet line A3 comprises the properties appropriate for its injection point back to the system.

In embodiments, an additive is prepared (partially or wholly) from styrene tar or crude streams comprising suitable oxidizable components via a tar oxidation unit 130/230. The oxidized stream (in additive component outlet line 137/237) can contain mixtures of oxidation products from components in the tar or crude streams in concentrations from about 10 ppm to 100,000 ppm (0.001 to 10 wt %) as an additive combination. In embodiments, the additive(s) in the oxidized stream can be injected to the feed stream 113/213 to the separation section 120/220 or any point therein. Without limitation, in such embodiments, the additive may be selected from: acetophenone, benzaldehyde, phenylethanol, and combinations thereof Features/Potential Advantages of the Herein-Disclosed Additive, Composition, System, and Method Herein described are additives comprising one or more chemical components that have a boiling point near that of DVB and that can also suppress insoluble polymer formation through active functional groups thereof. As crude styrene contains DVB, a potent cross-linking agent, which forms insoluble polymer when present during styrene polymerization, the herein-disclosed additives can be utilized to minimize the amount of insoluble polymer (i.e., polystyrene) formed during the production of styrene (e.g., during the purification of styrene monomer from a crude styrene stream). The one or more chemical components comprise one or more active functional groups comprising reactive organic species with oxygen, hydrogen, nitrogen and/or similar active sites. Such organic species include, without limitation, alcohols, aldehydes, ketones, acids, and labile hydrogen. Insoluble polymer fouling can reduce production, shorten run lengths and lengthen turnarounds. Thus, the additive, composition, system and method of this disclosure may provide for increased production, longer run lengths, and/or shortened turnaround times, in embodiments.

EXAMPLES

Example 1: Additive Performance for Insoluble Polymer Abatement

The ability of various additives to control insoluble polymer formation was tested. Performance evaluations were conducted in liquid phase using a 6-port test system. A common heating block with six ports that can hold 25(D)× 150(H) mm test tubes was utilized, thus allowing the simultaneous operation of six separate solutions. Each tube was sealed with a septum cap, and a common nitrogen header was used to purge each tube. Nitrogen purge was introduced into the test tubes using 1/16" tubing extending through the septum cap. A syringe needle was used to vent purge gas.

Test solutions containing about 60 weight percent (wt %) styrene were collected as crude styrene samples from lab adiabatic pilot units. The crude styrene was spiked with DVB to produce 0.1% (wt) concentration. The additives were used in the same concentration, 0.1% (wt). Crude styrene with 0.1% (wt) DVB was used as the reference sample. For the evaluation, 10 g of a solution was placed in a test tube and purged nitrogen at room temperature. The heating block was set at 120° C. and allowed to stabilize before introducing the test solutions. After purging each solution, each test tube was moved into the heating block ports. Samples were taken after 15 and 30 minutes. Each sample was analyzed by gas chromatography (GC) using a method that can measure low levels of DVB and quantitatively analyze the usual crude styrene species, including benzene, toluene, EB, styrene, DVB, ethyl-vinyl benzene and phenylacetylene. The test solutions were also tested gravimetrically for polymer and heavies using a solids analyzer comprising an electronic balance with a high intensity infrared lamp operable to evaporate monomer. The change in the DVB concentration (a decrease of which can correlate with insoluble polymer formation) and the soluble polymer formation were recorded.

The additives tested in this Example are listed in Table 1. Species to be tested were chosen based on their boiling, points, having boiling points higher than that of styrene and close to that of DVB. The boiling points of the additives tested are also shown in Table 1; styrene and DVB and their boiling points are included for reference.

TABLE 1

Selected Additives and Boiling Points Thereof for Screening Study at 120° C. using Crude Styrene

| Additive or Component | BP (° C.) |
|---|---|
| N,N-DiEt PDA | 268 |
| Biphenyl | 254 |
| Di-propylene glycol | 233 |
| Terpineol | 215 |
| Ethyl Benzoate | 212 |
| Tetralin | 207 |
| Acetophenone | 202 |
| Methyl Benzoate | 198 |
| DVB | 195 |
| Propylene Glycol | 189 |
| Ethyl Carbamate | 183 |
| Ethyl Acetoacetate | 181 |
| DPGME | 180 |
| Benzaldehyde | 178 |
| Styrene | 145 |

Figure 3:
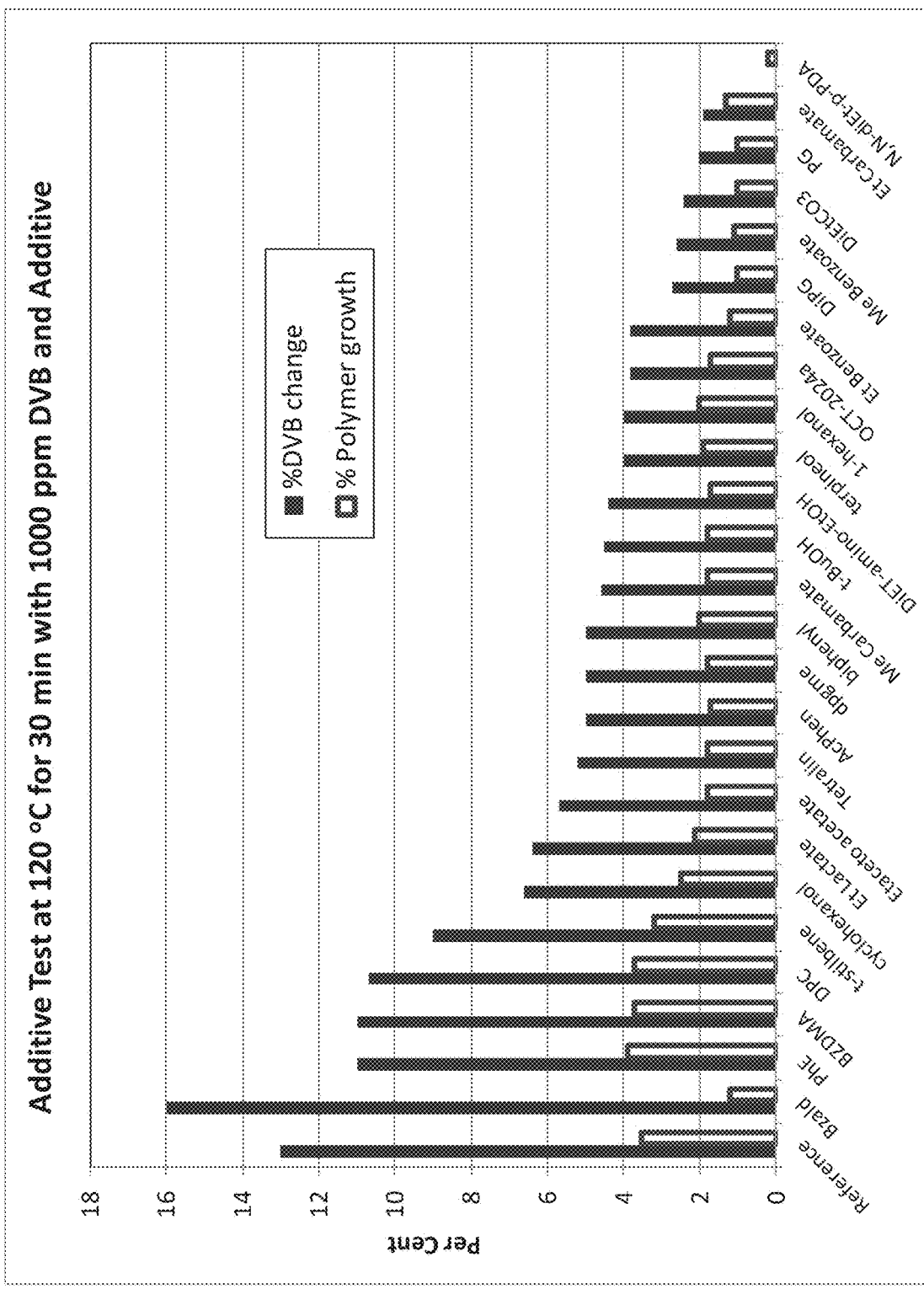
FIG. 3 is a bar graph of percent (%) DVB change and percent soluble polymer growth in batch testing of the additives of Example 1 and selected reference species.

The results for 1000 ppm of each additive after 30 minutes at 120° C. in crude styrene dosed with 1000 ppm of DVB are shown in FIG. 3, which is a bar graph of % DVB change and percent polymer growth for the additives of Example 1. (In FIG. 3, Bzald is benzaldehyde, PhE is 1-phenylethanol, BZDMA is benzaldehyde dimethyl acetal, DPC is diphenyl carbonate, ET Lactate is ethyl lactate, Etaceto acetate is ethylaceto acetate, AcPhen is acetophenone, dpgme is dipropylene glycol methyl ether, DiET-amino-EtOH is diethyl-amino ethanol, DiPG is dipropylene glycol, PG is propylene glycol, and N,N-diEt PDA is N,N-diethyl-1,4-phenylenediamine.)

Additives tested included N,N-diethylphenylenediamine, methyl carbamate, ethyl carbamate, methyl benzoate, ethyl benzoate, di-propylene glycol, diethylamino-ethanol, biphenyl, cyclohexanol, and ethylaceto-acetate; the functional groups of the active species tested included amines, amino-alcohols, labile C—C bonds, esters, and carbamates. Amines, glycols, benzoates and carbamates produced notably good results.

Figure 4:
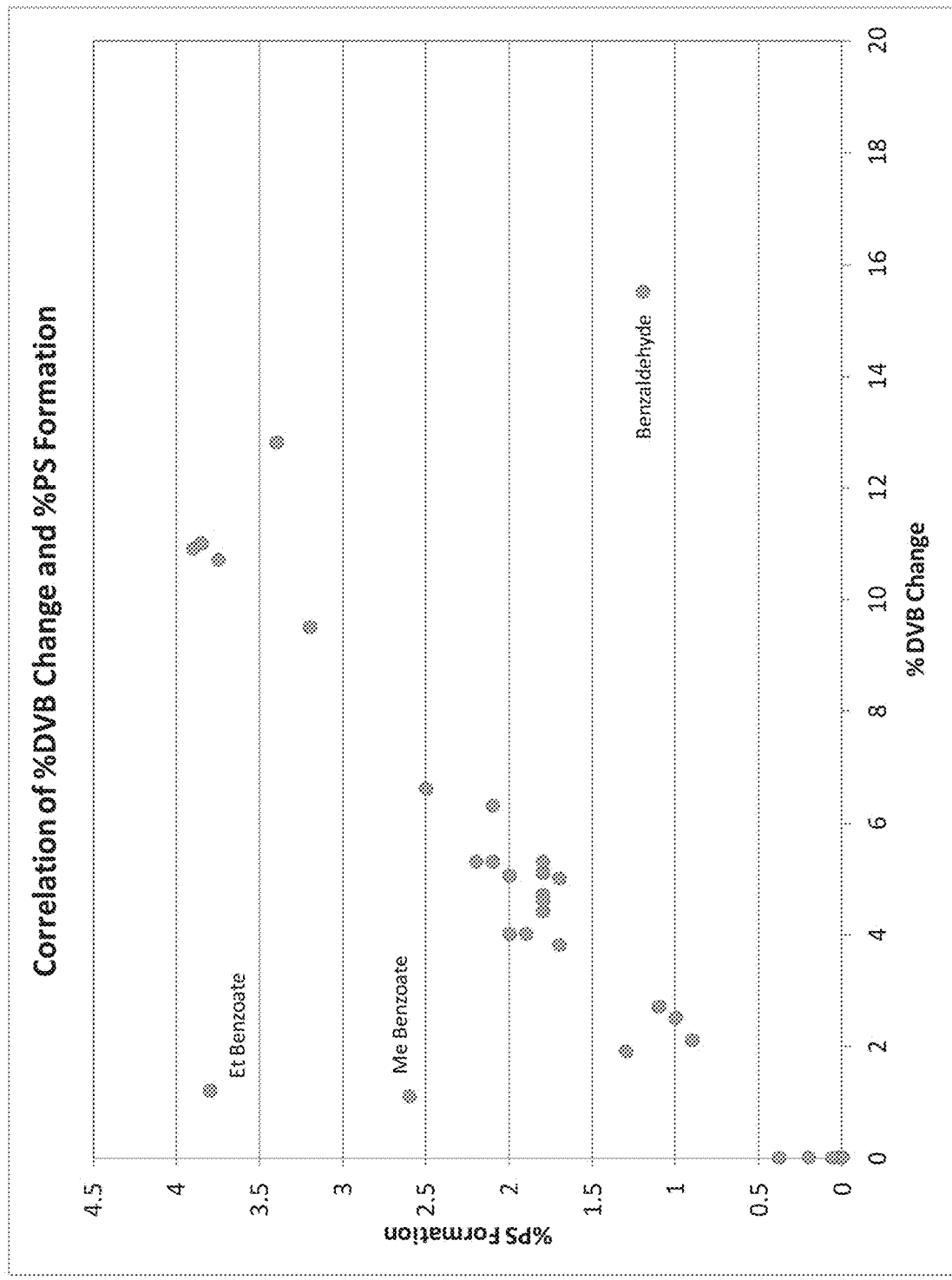
FIG. 4 is a plot of percent soluble polystyrene (PS) polymer formation and percent (%) DVB change for selected additives of Example 1.

Most additives evaluated showed correlation of their % PS formation and the % DVB change, suggesting they function by inhibiting the initiation and/or the propagation of styrene polymerization. This may be expected, as DVB is consumed by free radical polymerization; once polymerization takes place, DVB will be incorporated into the polymer. However, as discussed below, there were some exceptions to this correlation. The results of all additives in the trial are compiled in FIG. 4, which is a plot of percent soluble polystyrene (PS) polymer formation as a function of percent DVB change for the additives of Example 1.

Without wishing to be limited by theory, it is believed that benzaldehyde reacted with DVB to show a high consumption of DVB during the course of the test. Benzaldehyde also inhibited the formation of polymer. The two benzoate species also did not align with the correlation of the other species. Both the methyl benzoate and the ethyl benzoate showed small changes in % DVB. Ethyl benzoate showed no ability to inhibit polymer formation, while methyl benzoate showed moderate inhibiting performance. Again, without wishing to be limited by theory, this suggests some other interaction with DVB that prevents its incorporation into radical polymerization and cross-linking of polymer, and also suggests that benzoate derivatives may be mixed with standard anti-polymerization inhibitors to prevent DVB cross-linking by selectively suppressing its reaction.

Example 2: Crude Styrene Condensate Area Fouling Study

As noted hereinabove, a first major area of a styrene production plant for potential issues with insoluble polymer fouling/formation is the heat exchanger area where condensation of the gas phase reactor effluent is cooled and liquefied. This condensate area has sufficient temperature to initiate styrene polymerization, and the concentration of DVB can be sufficient to form insoluble polymer. DVB has a higher boiling point of 195° C. and liquefies before styrene during condensation; DVB can also thermally initiate polymerization. Accordingly, a testing apparatus was designed to mimic conditions where gas phase crude styrene and steam are condensed into liquids.

Figure 5:
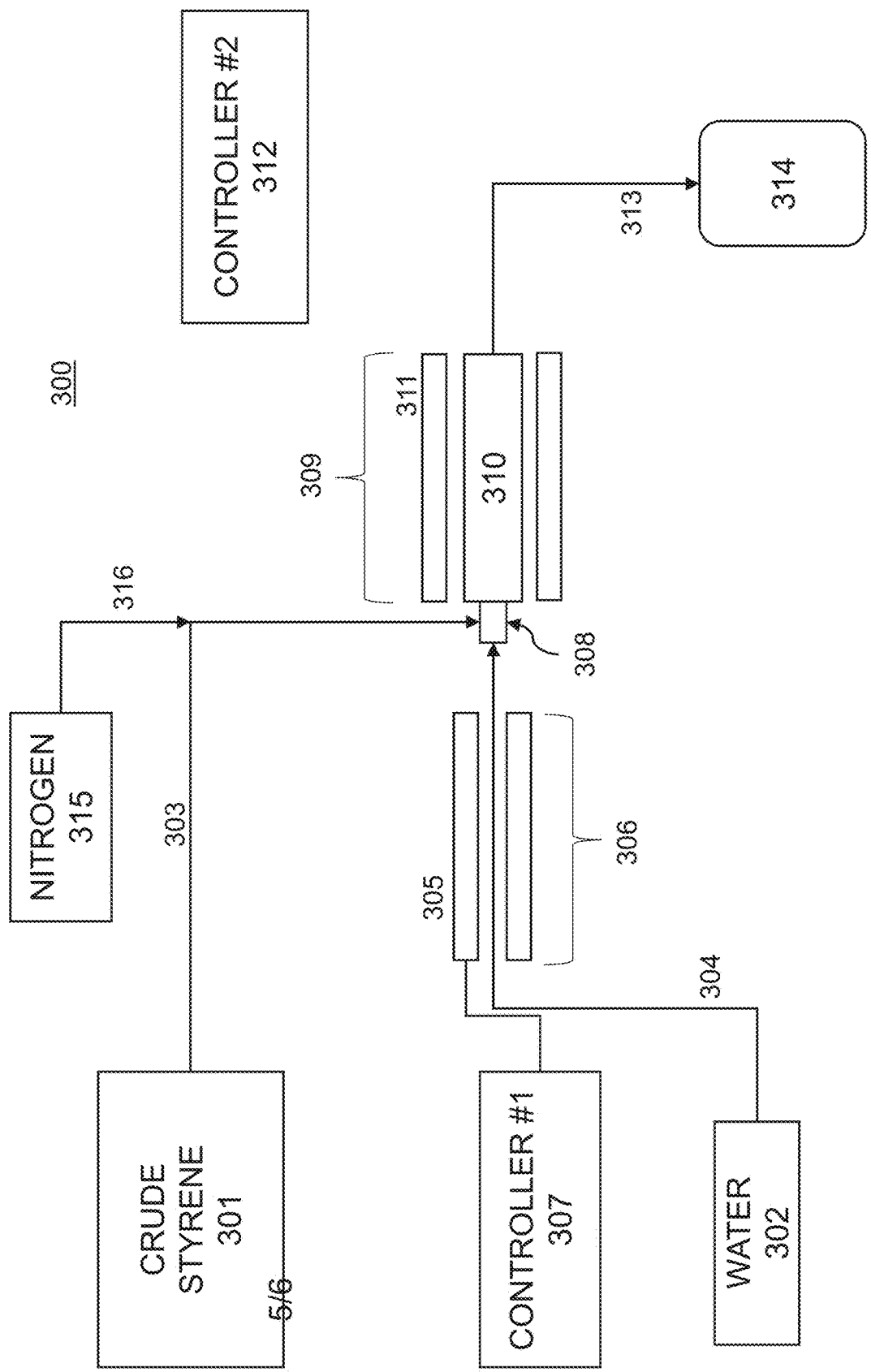
FIG. 5 is a schematic diagram of the crude styrene condensate test apparatus of Example 2.

A crude styrene feed was prepared from EB dehydrogenation lab reactor effluent comprising about 55-65 wt. % styrene, 35-45 wt % EB, 2 wt. % benzene/toluene, and trace by-products to which an additional 500 ppm of DVB was added. FIG. 5 is a schematic diagram of the crude styrene condensate test apparatus 300 of Example 2. ISCO syringe pumps 301 and 302 were used to add the crude styrene and water for steam creation, respectively, into the system. The main vessel 309 consisted of a horizontal tube 310, having dimensions of ½" inside diameter (ID) by 15" length, that was wrapped in heat tape 311 powered from an independent controller 312 set at 130° C. The water was fed via ⅛" tubing 304 to a pre-heat vaporization zone 306 controlled by independent controller 307 set at 135° C. to heat heat tape 305 connected to inlet 308 of the horizontal tube 310. The crude styrene was added via ⅛" tubing 303 with the steam at the inlet 308 of the horizontal tube 310. The effluent 313 passed through a water-cooled condenser (not shown) and into a sample collection or effluent bottle 314. Nitrogen was introduced via 90 PSI nitrogen utility line and regulator 315 and tubing 316 to purge horizontal tube 310 between experiments. The nitrogen was used remove oxygen before experiments and to clear the apparatus between experiments.

Individual experiments were conducted by adding selected additives to the crude styrene. Dosages listed are based on the hydrocarbon portion only, excluding the steam/water. Heat tapes 305 and 311 were started first and allowed to reach their set points (i.e., 135° C. and 130° C., respectively). The water pump was started at 0.25 mL/min and run until the system stabilized with only steam. The crude styrene pump was then started at 0.5 mL/min. Tubing 310 of main vessel 309 maintained a temperature in the range of 110° C. to 140° C. Most experiments were conducted at 110° C. or 130° C. The data from the 130° C. experiments was used to select the acceptable additives. After four hours, a composite effluent sample was collected and analyzed by GC along with a crude styrene feed sample. The change in DVB (weight percent loss by GC) in concentration from the feed to the effluent was reported; the greater the loss of DVB, the more insoluble polymer is presumed formed. The formation of insoluble polymer was confirmed by inspection of the horizontal tube after experiments were conducted.

Figure 6:
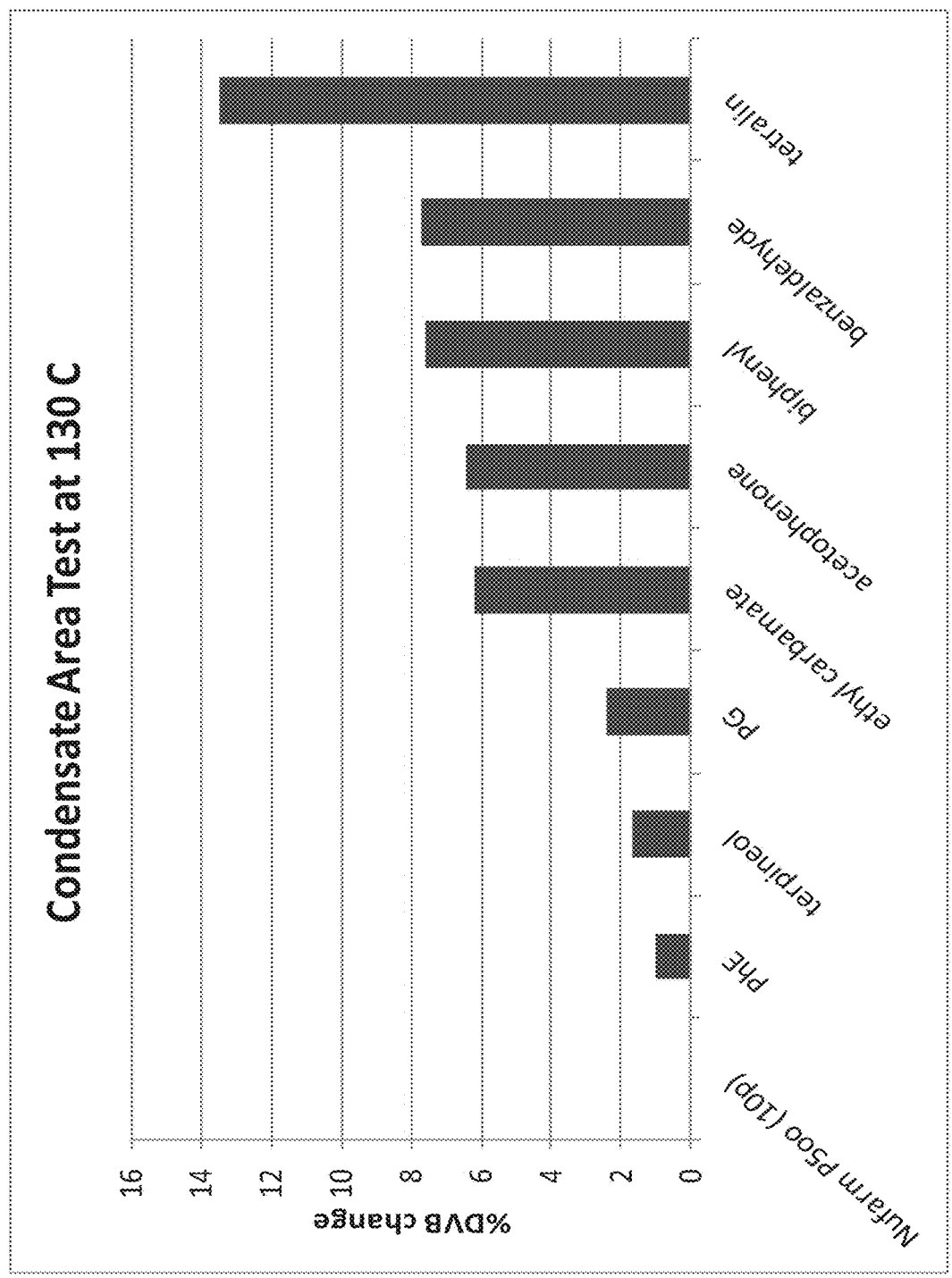
FIG. 6 is a bar graph of the percent (%) DVB change for the condensate testing results of Example 2.

Several candidates with appropriate physical properties were evaluated via the crude styrene condensate test apparatus described above, and the condensate additive testing data obtained are shown Table 2 below and in FIG. 6, which is a bar graph of the percent DVB change for the condensate testing results of Example 2.

The additives were tested at 200 ppm dosages. PhE (phenylethol), terpineol and PG (propylene glycol) showed high performance while ethyl carbamate, acetophenone, biphenyl and benzaldehyde produced intermediate performance. Tetralin had low activity in this first testing area (A1), and is included mainly for comparison.

TABLE 2

Results from Example 2

| Additive | PPM | Tube T (° C.) | WT. % DVB Change |
|---|---|---|---|
| diethanolamine | 200 | 130 | 0.76 |
| 3-amino-1-propanol | 200 | 130 | 0.40 |
| 1-Phenylethanol (PhE) | 200 | 130 | 1 |
| Terpineol | 200 | 130 | 1.7 |
| Propylene Glycol (PG) | 200 | 130 | 2.4 |
| Ethyl Carbamate | 200 | 130 | 6.2 |
| Acetophenone | 200 | 130 | 6.4 |
| Biphenyl | 200 | 130 | 7.6 |
| Benzaldehyde | 200 | 130 | 7.7 |
| Tetralin | 200 | 130 | 13.5 |

This Example studied the performance of additives for the condensate region of a styrene production plant at the point where high-temperature, gaseous reactor effluent is converted to liquid. At this ('first area') location, steam is present and a steep temperature gradient is found. The suspected primary cause of the fouling seen in this area is the higher boiling point of DVB that could result in hot, liquid DVB condensing before styrene/EB, and thus initiating insoluble polymer formation. Commercial inhibitors have a very high boiling point and would condense before DVB but many may have thermal instabilities if higher temperatures, such as those encountered here, are present. Also such commercial products could be expensive for use in this application. A readily-available, inexpensive compound with chemical activity and a boiling point near that of DVB, such as the additives of this disclosure, provide an attractive option for solving this problem.

Additional Description

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The following are nonlimiting, specific embodiments in accordance with the present disclosure:

A: A method of reducing the fouling in a process for the production of styrene, the method comprising: introducing an additive into a stream comprising styrene and byproduct divinyl benzene (DVB), wherein the additive comprises: at least one chemical compound comprising one or more functional groups selected from amines, alcohols, aminoalcohols, labile C—C, esters, carbamates, aldehydes, ketones, acids, acetates, benzoates, labile hydrogen, and combinations thereof, and having a boiling point greater than or equal to 170° C. and within 10, 20, 30, 40, 50, or 60° C. of the boiling point of divinyl benzene (DVB) (which is 195° C.), wherein the at least one chemical compound is active to inhibit divinyl benzene (DVB) crosslinking.

B: An additive for reducing the fouling in a process for the purification of a crude styrene comprising styrene and byproduct divinyl benzene (DVB), the additive comprising: at least one chemical compound comprising one or more functional groups active to inhibit divinyl benzene (DVB) crosslinking, and having a boiling point greater than or equal to 170° C. and within 10, 20, 30, 40, 50, or 60° C. of the boiling point of DVB, which is 195° C.; and a polymerization inhibitor having a boiling point of greater than that of the at least one chemical compound.

C: A composition comprising: a crude styrene stream comprising styrene and by-product divinyl benzene (DVB); and an additive comprising at least one chemical compound comprising one or more functional groups active to inhibit DVB crosslinking, and having a boiling point in the range of from 170° C. to 270° C., from 170° C. to 230° C., from 170° C. to 220° C., or from 170° C. to 195° C.

D: A system for the production of styrene via dehydrogenation of ethylbenzene (EB), the system comprising: one or more dehydrogenation reactors operable to contact EB and steam with a dehydrogenation catalyst under dehydrogenation conditions to yield a crude styrene effluent comprising styrene and byproduct divinyl benzene (DVB); a heat exchange apparatus configured to reduce the temperature of the crude styrene effluent; a separations apparatus configured to separate offgas and condensate from the cooled crude styrene effluent and thus provide a dehydrogenation mixture; a distillation section operable to separate the dehydrogenation mixture into one or more streams comprising benzene, toluene, ethylbenzene, or a combination thereof, a tar stream, and a stream comprising styrene; an oxidation unit configured to produce, via oxidation of the tar stream, at least one chemical compound comprising one or more functional groups active to inhibit divinyl benzene crosslinking, and having a boiling point greater than or equal to 170° C. and within 10, 20, 30, 40, 50, or 60° C. of the 195° C. boiling point of DVB; and one or more recycle lines whereby the at least one chemical compound can be combined with the crude styrene effluent, the cooled crude styrene effluent, the dehydrogenation mixture, a feed, recycle, or reflux to a distillation column of the distillation section, or a combination thereof.

E: A method of reducing the fouling in a process for the production of styrene, the method comprising: producing, via oxidation of a crude styrene, a styrene tar stream, or a combination thereof, at least one chemical compound active to inhibit divinyl benzene (DVB) crosslinking, comprising one or more functional groups selected from amines, alcohols, amino-alcohols, labile C—C, esters, carbamates, aldehydes, ketones, acids, acetates, benzoates, labile hydrogen, and combinations thereof, and having a boiling point greater than or equal to 170° C. and within 10, 20, 30, 40, 50, or 60° C. of the boiling point of divinyl benzene (DVB) (which is 195° C.); and introducing the at least one chemical compound into a stream comprising styrene and byproduct divinyl benzene (DVB), whereby divinyl benzene (DVB) crosslinking is inhibited.

Each of the embodiments A, B, C, D, and E may have one or more of the following additional elements: Element 1: wherein the at least one chemical compound has a boiling point of less than or equal to about 250° C., 240° C., 230° C., 220° C., 210° C., 200° C., or 195° C., a boiling point of greater than or equal to about 170° C., 180° C., 190° C., 200° C., 210° C., 220° C., or 230° C., or a combination thereof. Element 2: wherein the at least one chemical compound is selected from amines, glycols, benzoates, carbamates, or combinations thereof. Element 3: wherein the at least one chemical compound comprises ethyl lactate, tetralin, acetophenone, propylene glycol, di-propylene glycol, dipropylene glycol methyl ether, transtilbene, N,N-diethyl-1,4,-phenylenediamine, phenylethanol (e.g., 1-phenylethanol), benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, or a combination thereof. Element 4: wherein the additive is introduced at a concentration of 0.001, 0.01 or 0.1 weight percent of the stream. Element 5: wherein the process for the production of styrene comprises an ethylbenzene (EB) dehydrogenation process. Element 6: wherein the stream comprising styrene and DVB into which the additive is introduced is a crude styrene effluent of an EB dehydrogenation reactor. Element 7: wherein the stream comprising styrene and DVB into which the additive is introduced is a feed, recycle, or reflux stream to a distillation column downstream of an EB dehydrogenation reactor. Element 8: wherein the distillation column comprises a distillation column configured for the separation of a tops product comprising EB from a bottoms product comprising styrene, a distillation column configured for the separation of a tops product comprising benzene and toluene from a bottoms product comprising EB and styrene, or a distillation column configured for the separation of a tops product comprising styrene from a bottoms product comprising tar. Element 9: wherein reducing the fouling comprises a reduction in the formation of insoluble polystyrene, soluble polystyrene, or both, of at least 1, 10, 50, or 100% relative to the same process absent the additive. Element 10: wherein the additive further comprises a polymerization inhibitor having a boiling point of above 195° C., 200° C., 250° C., or 300° C. Element 11: wherein the polymerization inhibitor is selected from dinitrophenols (e.g., DNOC (di-nitro-ortho-cresol) or DNBP (di-nitro-sec-butyl-phenol)), TMPO compounds (e.g., 4-hydroxy-2,2,6,6-tetramethylpiperidine 1-oxyl), oximes (e.g., alternative retarder), or a combination thereof. Element 12: wherein the polymerization inhibitor has a boiling point of greater than 195° C., 200° C., 250° C., or 300° C. Element 13: wherein the one or more functional groups are selected from amines, alcohols, amino-alcohols, labile C—C, esters, carbamates, aldehydes, ketones, acids, acetates, benzoates, labile hydrogen, glycols or combinations thereof. Element 14: wherein the at least one chemical compound has a boiling point of less than or equal to about 250° C., 240° C., 230° C., 220° C., 210° C., 200° C., or 195° C., has a boiling point of greater than or equal to about 170° C., 180° C., 190° C., 200° C., 210° C., 220° C., or 230° C., or a combination thereof. Element 15: wherein the crude styrene is a product of ethylbenzene (EB) dehydrogenation. Element 16: further comprising a polymerization inhibitor having a boiling point greater than that of the at least one chemical compound. Element 17: wherein the crude styrene stream comprises a crude styrene effluent from an ethylbenzene (EB) dehydrogenation reactor. Element 18: wherein the crude styrene stream comprises a feed, recycle, or reflux stream to a distillation column downstream of an ethylbenzene (EB) dehydrogenation reactor. Element 19: wherein the at least one chemical compound comprises benzaldehyde, acetophenone, phenylethanol, or a combination thereof.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed is:

1. A method of reducing the fouling in a process for the production of styrene, the method comprising:
   introducing an additive into a stream comprising styrene and byproduct divinyl benzene (DVB), wherein the additive comprises: at least one chemical compound, comprising ethyl lactate, tetralin, acetophenone, propylene glycol, di-propylene glycol, dipropylene glycol methyl ether, trans-stilbene, phenylethanol, benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, or a combination thereof, wherein the at least one chemical compound is active to inhibit divinyl benzene (DVB) crosslinking.

2. The method of claim 1, wherein the at least one chemical compound has a boiling point ranging from about 170° C. to about 230° C.

3. The method of claim 1, wherein the additive is introduced at a concentration of 0.001, 0.01 or 0.1 weight percent of the stream.

4. The method of claim 1, wherein the process for the production of styrene comprises an ethylbenzene (EB) dehydrogenation process.

5. The method of claim 4, wherein the stream comprising styrene and DVB into which the additive is introduced is a crude styrene effluent of an EB dehydrogenation reactor.

6. The method of claim 4, wherein the stream comprising styrene and DVB into which the additive is introduced is a feed, recycle, or reflux stream to a distillation column downstream of an EB dehydrogenation reactor.

7. The method of claim 6, wherein the distillation column comprises a distillation column configured for the separation of a tops product comprising EB from a bottoms product comprising styrene, a distillation column configured for the separation of a tops product comprising benzene and toluene from a bottoms product comprising EB and styrene, or a distillation column configured for the separation of a tops product comprising styrene from a bottoms product comprising tar.

8. The method of claim 1, wherein reducing the fouling comprises a reduction in the formation of insoluble polystyrene, soluble polystyrene, or both, of at least 1, 10, 50, or 100% relative to the same process absent the additive.

9. The method of claim 1, wherein the additive further comprises a polymerization inhibitor having a boiling point of above 195° C., 200° C., 250° C., or 300° C.

10. The method of claim 9, wherein the polymerization inhibitor is selected from dinitrophenols, TEMPO compounds, oximes, or a combination thereof.

11. A method of reducing the fouling in a process for the production of styrene, the method comprising:
    producing via oxidation of a crude styrene, a styrene tar stream, or a combination thereof, at least one chemical compound active to inhibit divinyl benzene (DVB) crosslinking, the at least one chemical compound comprises ethyl lactate, tetralin, acetophenone, propylene glycol, di-propylene glycol, dipropylene glycol methyl ether, trans-stilbene, N,N-diethyl-1,4,-phenylenediamine, phenylethanol, benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, or a combination thereof; and
    introducing the at least one chemical compound into a stream comprising styrene and byproduct divinyl benzene (DVB), whereby divinyl benzene (DVB) crosslinking is inhibited.

12. A system for the production of styrene via dehydrogenation of ethylbenzene (EB), the system comprising:
    one or more dehydrogenation reactors operable to contact EB and steam with a dehydrogenation catalyst under dehydrogenation conditions to yield a crude styrene effluent comprising styrene and byproduct divinyl benzene (DVB);
    a heat exchange apparatus configured to reduce temperature of the crude styrene effluent;
    a separations apparatus configured to separate offgas and condensate from the cooled crude styrene effluent and thus provide a dehydrogenation mixture;
    a distillation section operable to separate the dehydrogenation mixture into one or more streams comprising benzene, toluene, ethylbenzene, or a combination thereof, a tar stream, and a stream comprising styrene;
    an oxidation unit configured to produce, via oxidation of the tar stream, at least one chemical compound comprising ethyl lactate, tetralin, acetophenone, propylene glycol, di-propylene glycol, dipropylene glycol methyl ether, transtilbene, phenylethanol, benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, or a combination thereof; and
    one or more recycle lines whereby the at least one chemical compound can be combined
    with the crude styrene effluent, the cooled crude styrene effluent, the dehydrogenation mixture, a feed, recycle, or reflux to a distillation column of the distillation section, or a combination thereof.

13. The system of claim 12, wherein the at least one chemical compound comprises benzaldehyde, acetophenone, phenylethanol, or a combination thereof.

* * * * *